US00PP14016P29

(12) United States Plant Patent
Kraan

(10) Patent No.: US PP14,016 P2
(45) Date of Patent: Jul. 22, 2003

(54) ROSA PLANT NAMED 'BOKRARUG'

(75) Inventor: Kees Jan Kraan, Boskoop (NL)

(73) Assignee: Boot and Company, Boskoop (NL)

( * ) Notice: Subject to any disclaimer, the term of this patent is extended or adjusted under 35 U.S.C. 154(b) by 0 days.

(21) Appl. No.: 10/121,160

(22) Filed: Apr. 11, 2002

(51) Int. Cl.[7] ..... A01H 5/00

(52) U.S. Cl. ..... Plt./103

(58) Field of Search ..... Plt./103

(56) References Cited

PUBLICATIONS

UPOV ROM GTITM Computer Database, GTI JOUVE Retrieval Software 2002/02, citation(s) for 'Bokrarug'.*

* cited by examiner

*Primary Examiner*—Bruce R. Campell
*Assistant Examiner*—W C Haas
(74) *Attorney, Agent, or Firm*—Mark P. Bourgeois

(57) ABSTRACT

A new cultivar of Rosa plant named 'Bokrarug' that is characterized by a compact and flattened globose habit, glossy dark green foliage, cream-yellow buds and white flowers. In combination these traits set 'Bokrarug' apart from all other existing varieties of Rosa known to the inventor.

1 Drawing Sheet

Botanical classification: Rosa.
Variety denomination: 'Bokrarug'.

BACKGROUND OF THE INVENTION

The present invention relates to a new and distinct cultivar of Rose plant botanically known as Rosa and hereinafter referred to by the cultivar name 'Bokrarug'.

The new cultivar is the product of a breeding program conducted by the inventor in a cultivated area of Boskoop, The Netherlands. The objective of the breeding program was to develop a new single-flowered rose with white flowers and a globose habit. 'Bokrarug' is a hybrid that originated from the induced hybridization of the female or seed parent Rosa 94207-15 (not patented) and the male or pollen parent Rosa 93511-02 (not patented). The cultivar 'Bokrarug' was selected by the inventor in 1997 as a plant within the progeny of the stated cross in a controlled environment of Boskoop, The Netherlands.

The closest comparison plant is Rosa 'Ivtagolf' (U.S. Plant Pat. No. 11,371) 'Bokrarug' is distinguishable from 'Ivtagolf' by larger darker leaves, larger flowers, and cream-yellow buds. The new cultivar 'Bokrarug' is distinguishable from the female parent Rosa 94207-15 by pure-white flowers and by its decreased susceptibility to black spot. The new cultivar 'Bokrarug' is distinguishable from the male parent Rosa 93511-02 by larger leaves and larger flowers. The female parent and the male parent are no longer in existence. Both were destroyed after their use for hybridization.

Asexual reproduction by cuttings of the new cultivar 'Bokrarug' were taken in 1999 in Boskoop, The Netherlands by the inventor. Since that time, under careful observation, the unique characteristics of the new Rose cultivar have been uniform, stable and reproduced true to type in successive generations of asexual reproduction.

SUMMARY OF THE INVENTION

The following represent the distinguishing characteristics of the new Rosa cultivar 'Bokrarug'. These traits in combination distinguish 'Bokrarug' as a new and distinct cultivar apart from all other existing varieties of Rosa known to the inventor. 'Bokrarug' has not been tested under all possible conditions and phenotypic differences may be observed with variations in environmental, climatic, and cultural conditions, however, without any variance in genotype.

1. Rosa 'Bokrarug' exhibits dark green glossy leaves.
2. Rosa 'Bokrarug' exhibits a compact, flattened globose habit.
3. Rosa 'Bokrarug' is hardy to USDA Zone 6.
4. Rosa 'Bokrarug' exhibits pure-white flowers.
5. Rosa 'Bokrarug' exhibits cream-yellow flower buds.

BRIEF DESCRIPTION OF THE DRAWING

The accompanying drawing illustrates the distinguishing traits of Rosa 'Bokrarug'. The plant in the drawing is three-years-old and was field grown in a two-litre container. The drawing on sheet 1 illustrates the plant in bloom and bud. The photograph was taken using conventional techniques and although colors may appear different from actual colors due to light reflectance it is as accurate as possible by conventional photographic techniques.

BOTANICAL DESCRIPTION OF THE PLANT

The following is a detailed description of the new Rosa cultivar named 'Bokrarug'. Data was collected in Boskoop, The Netherlands from three-year-old field grown plants in two-litre containers. The time of year was August and the temperatures ranged from 14–27° Centigrade during the day, and 6–12° Centigrade during the night. The light level was natural outdoor light and there were no photoperiodic treatments or growth retardants used. Color determinations are in accordance with The Royal Horticultural Society Colour Chart except where general color terms of ordinary dictionary significance are used. The growing requirements are similar to the species.

Botanical classification: Rosa 'Bokrarug'.
Type: Perennial shrub.

Use: Ornamental.
Parentage: 'Bokrarug' is a hybrid plant that resulted from the induced hybridization of the following parent plants:
*Female parent.*—Rosa 94207-15 (not patented).
*Male parent.*—Rosa 93511-02 (not patented).
Vigor: Moderate.
Growth rate: Approximately 15 cm. per month in spring.
Growth habit: Compact.
Plant shape: Globose.
Suitable container size: 1–2 litre container.
Height: 1 meter in height.
Width: 1.20 meters in width.
Hardiness: USDA Zone 6.
Propagation: Softwood cuttings.
Time to initiate roots: Approximately 60 days are required to produce roots on an initial cutting.
Crop time: Approximately 14 months are required to achieve a finished plant from an unrooted cutting.
Root system: Fine and fibrous.
Light: Plant in full sun.
Soil: Plant in moist but well drained soil.
Seasonal interest: White flowers in spring.
Stem:
*Branching habit.*—Basal branching and lateral branches with terminal inflorescences.
*Average number of lateral branches.*—Four.
*Stem diameter.*—Approximately 3 mm. in diameter.
*Stem length.*—Approximately 12 cm. in length.
*Stem strength.*—Strong.
*Stem color.*—143A.
*Pubescence.*—Absent.
*Internode length.*—Approximately 3 cm. between nodes.
*Shape.*—Cylindrical.
*Surface.*—Glabrous and dull and covered with sharp spines.
*Number of spines.*—0.4 per square cm.
*Spine dimensions.*—Approximately 9 mm. in length and 7 mm. in width.
*Color of spines.*—Color ranges from 178C to 152A.
Foliage:
*Durability to foliage stresses.*—High.
*Texture.*—Smooth and glossy.
*Leaf arrangement.*—Alternate.
*Compound or single.*—Compound.
*Quantity of leaves per lateral branch.*—Approximately 6.
*Quantity of leaflets per leaf.*—Seven (5 near the inflorescence).
*Leaf margin.*—Serrate.
*Pubescence.*—Absent.
*Stipules.*—Present.
*Stipule dimensions.*—1.6 cm. in length and 3 mm. in width.
*Stipule color.*—141B.
*Stipule apex.*—Acuminate.
*Stipule margins.*—Lacerate.
*Vein pattern.*—Pinnate.
*Vein color* (*abaxial surface*).—144C.
*Vein color* (*adaxial surface*).—144B.
*Leaf shape.*—Elliptic.
*Leaf apex.*—Acute to shallowly apiculate.
*Leaf base.*—Rounded.
*Leaf attachment.*—Petiolate.
*Petiole dimensions.*—2.1 cm. in length and 1.25 mm. in width.
*Petiole color.*—144B.
*Rachis color.*—143B.
*Other.*—Average of 6 sharp spines at base of rachis that are 2 mm. in length and 170B in color.
*Leaf length.*—12 cm. in length.
*Leaf width.*—7.5 cm. in width.
*Leaflet length.*—4.2 cm. in length.
*Leaflet width.*—2.4 cm. in width.
*Young leaf color* (*abaxial surface*).—146B.
*Young leaf color* (*adaxial surface*).—146A.
*Mature leaf color* (*abaxial surface*).—137B.
*Mature leaf color* (adaxial surface).—139A.
Flower:
*Flower arrangement.*—Compound terminal corymb.
*Inflorescence type.*—Compound terminal corymb.
*Inflorescence height.*—Approximately 15 cm. in height.
*Inflorescence diameter.*—Approximately 14 cm. in diameter.
*Quantity of flowers per inflorescence.*—Approximately 45.
*Flower type.*—Single.
*Flowering habit.*—Repeat flowering from late May to the end of October.
*Quantity of flowers per lateral stem.*—Approximately 100.
*Quantity of flower buds per lateral stem.*—Approximately 100.
*Quantity of flowers and buds per plant.*—Approximately 600.
*Flowering season.*—Late spring to autumn.
*Time to flower* (*response time*).—Approximately 6 months.
*Rate of flower opening.*—Approximately 20% of the flowers per corymb are opened at once.
*Fragrance.*—Mild perfume scent.
*Flower bud length.*—1.6 cm. in length.
*Flower bud diameter.*—1 cm. in diameter.
*Flower bud shape.*—Ovate.
*Bud color.*—18B.
*Flower aspect.*—Upward to outward.
*Flower shape.*—Rotate.
*Flower dimensions.*—5.5 cm. in diameter and 2 cm. in height.
*Flower longevity.*—Lasts approximately 10 days on plant.
*Petal color when opening* (*under side*).—Mostly white 155A with a yellow base of 5C.
*Petal color when opening* (*upper side*).—Mostly white 155A with a yellow base of 5C.
*Petal color fully opened* (*upper side*).—Mostly white 155C with a yellow base of 4C.
*Petal color fully opened* (*under side*).—Mostly white 155C with a yellow base of 4D.
*Petal appearance.*—Dull.
*Petal texture.*—Glabrous.
*Petal arrangement.*—Rotate.
*Number of petals.*—Five in number.
*Petals fused or unfused.*—Unfused.
*Petal shape.*—Broad obovate.
*Petal margin.*—Entire.
*Petal apex.*—Shallowly retuse.
*Petal dimensions.*—2.6 cm. in length and 2.5 cm. in width.
*Petaloids.*—Absent.
*Self-cleaning or persistent.*—Self-cleaning.
*Peduncle strength.*—Strong.

*Peduncle color.*—143A.
*Peduncle dimensions.*—3.6 cm. in length and 2.5 mm. in diameter.
*Peduncle angle.*—0–50°.
*Pedicels.*—Present.
*Pedicel dimensions.*—1.5 cm. in length and 1.5 mm. in diameter.
*Pedicel angle.*—0–50°.
*Pedicel color.*—143C.
*Sepal color* (*upper side*).—137B.
*Sepal color* (*under side*).—141A.
*Sepal surface.*—Dull and pubescent.
*Sepal arrangement.*—Rotate and reflexed.
*Number of sepals.*—Five.
*Sepal shape.*—Lanceolate.
*Sepal margin.*—Mostly entire but can have one incision on each side.
*Sepal apex.*—Caudate.
*Sepal base.*—Broad cuneate.
*Sepal dimensions.*—1.9 cm. in length and 6 mm. in width.
*Petaloids.*—Absent.
*Calyx shape.*—Rotate and reflexed.
*Calyx dimensions.*—1.9 cm. in length and 1.4 cm. in diameter.

Reproduction organs:
*Stamen number.*—Approxiamtely 75.
*Anther shape.*—Irregular kidney shape.
*Anther attachment.*—Dorsifixed.
*Anther dimensions.*—1.5 mm. in diameter and 1.5 mm. in length.
*Anther color.*—17A.
*Amount of pollen.*—Low.
*Pollen color.*—14A.
*Pistil number.*—16 in number.
*Pistil dimensions.*—5 mm. in length and 1.5 mm. in diameter.
*Stigma shape.*—Irregular and flattened.
*Stigma color.*—151B.
*Style dimensions.*—3.5 mm. in length and 1.5 mm. in diameter.
*Style color.*—151B.
*Ovary color.*—143B.

Seed: Seed production has not been observed.

I claim:

1. A new and distinct variety of Rosa plant named 'Bokrarug' as described and illustrated.

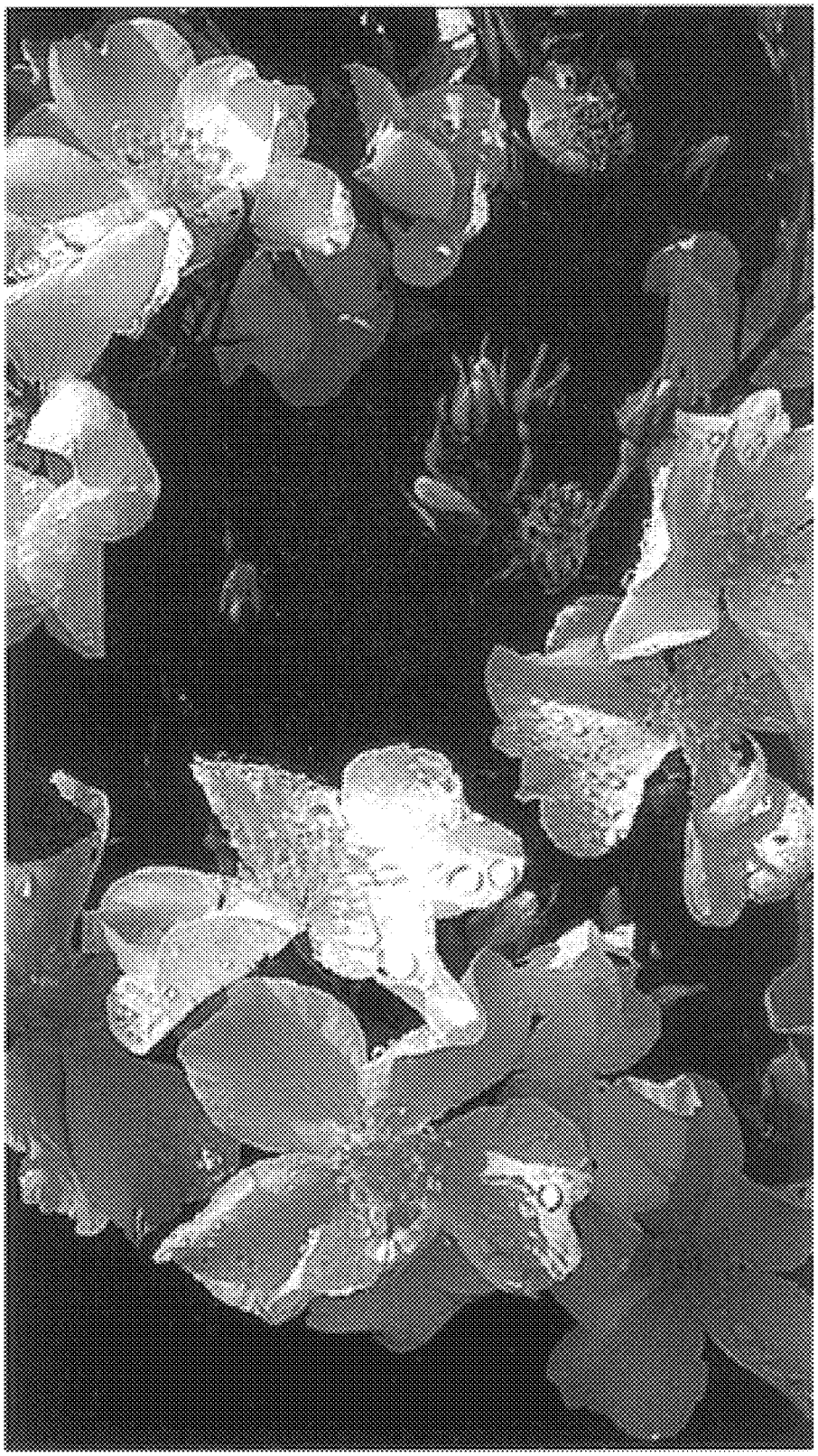

* * * * *